(12) United States Patent
Sharpe et al.

(10) Patent No.: US 12,668,563 B2
(45) Date of Patent: Jun. 30, 2026

(54) PROCESS FOR DEPOLYMERIZATION OF A POLY(C2-C4 ALKYLENE TEREPHTHALATE)

(71) Applicant: Eastman Chemical Company, Kingsport, TN (US)

(72) Inventors: Robert Jacks Sharpe, Madison, AL (US); Michael Charles Morrow, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 893 days.

(21) Appl. No.: 17/757,394

(22) PCT Filed: Dec. 10, 2020

(86) PCT No.: PCT/US2020/064255
§ 371 (c)(1),
(2) Date: Jun. 15, 2022

(87) PCT Pub. No.: WO2021/126661
PCT Pub. Date: Jun. 24, 2021

(65) Prior Publication Data
US 2023/0030777 A1 Feb. 2, 2023

Related U.S. Application Data

(60) Provisional application No. 62/951,425, filed on Dec. 20, 2019.

(51) Int. Cl.
| | |
|---|---|
| *C07C 67/03* | (2006.01) |
| *C07C 67/54* | (2006.01) |
| *C07C 69/82* | (2006.01) |
| *C08J 11/22* | (2006.01) |
| *C08J 11/28* | (2006.01) |

(52) U.S. Cl.
CPC .............. *C07C 67/03* (2013.01); *C07C 67/54* (2013.01); *C07C 69/82* (2013.01); *C08J 11/22* (2013.01)

(58) Field of Classification Search
CPC . C07C 67/03; C07C 69/82; C08J 11/16; C08J 11/28; Y02W 30/62
See application file for complete search history.

(56) References Cited

U.S. PATENT DOCUMENTS

| | | | |
|---|---|---|---|
| 3,037,050 A | 5/1962 | Erlenback et al. | |
| 3,321,510 A | 5/1967 | Lotz et al. | |
| 3,448,298 A | 6/1969 | Peterson | |
| 3,776,945 A | 12/1973 | Ligorati et al. | |
| 4,163,890 A | 8/1979 | Terai et al. | |
| 4,578,502 A | 3/1986 | Cudmore | |
| 5,051,528 A | 9/1991 | Naujokas et al. | |
| 5,498,749 A | 3/1996 | Heise et al. | |
| 2012/0223270 A1* | 9/2012 | Alabdulrahman | ...... C07C 67/03 560/64 |
| 2017/0008826 A1* | 1/2017 | Essaddam | ............. C07C 29/095 |

FOREIGN PATENT DOCUMENTS

| | | | | |
|---|---|---|---|---|
| JP | S36-009425 | * | 7/1961 | |
| JP | H07 309808 A | | 11/1995 | |
| JP | 2004 250414 A | | 9/2004 | |
| JP | 2011 207823 | | 10/2011 | |
| JP | 2014058476 | * | 4/2014 | ............. C07C 67/03 |

OTHER PUBLICATIONS

Mishra, S., et al., Kinetic and thermodynamic study of methanolysis of poly(ethylene terephthalate) waste powder, Polymer International, vol. 52, issue 3, pp. 337-342 (Year: 2003).*
Notification of Transmittal of the International Search Report and the Written Opinion of the International Searching Authority, or the Declaration date of mailing Mar. 18, 2021 received in International Application No. PCT/US2020/064255.
Fukushima, Kazuki et al.; Organocatalytic Depolymerization of Poly(ethylene terephthalate); , Journal Polymer Science, Part A Polymer Chemistry, 49, 2011; pp. 1273-1281.
Fukushima, Kazuki et al.; "Unexpected efficiency of cyclic amidine catalysts in depolymerizing poly(ethylene terephthalate)"; Journal Polymer Science, Part A Polymer Chemistry, 51; 2013, pp. 1606-1611.
George, Neena and Kurian, Thomas; "Recent Developments in the Chemical Recycling of Postconsumer Poly(ethylene terephthalate) Waste"; Industrial & Engineering Chemistry Research 2014 53 (37), pp. 14185-14198.
Venkatachalam, S. et al.; "Chapter 4: Degradation and Recyclability of Poly (Ethylene Terephthalate)"; Polyester, 2012, pp. 75-98.

* cited by examiner

*Primary Examiner* — Yate' K Cutliff
(74) *Attorney, Agent, or Firm* — Tammye L. Taylor Polk

(57) ABSTRACT

Provided is a process for depolymerization of a poly($C_2$-$C_4$ alkylene terephthalate), which comprises contacting a poly($C_2$-$C_4$ alkylene terephthalate) with methanol and a catalyst chosen from potassium carbonate, sodium carbonate, magnesium methoxide, 1,8-diazabicyclo[5.4.0]undec-7-ene, and triazabicyclodecene, at a temperature sufficient to effect said depolymerization. The process of the invention can be carried out a substantially lower temperature and requires less methanol than necessary for zinc acetate-catalyzed reactions, and is sufficiently robust to tolerate lower-quality poly($C_2$-$C_4$ alkylene terephthalate) scrap feeds.

9 Claims, No Drawings

PROCESS FOR DEPOLYMERIZATION OF A POLY(C2-C4 ALKYLENE TEREPHTHALATE)

CROSS-REFERENCE TO RELATED APPLICATION(S)

This application is a national stage filing under 35 USC § 371 of International Application Number PCT/US2020/064255, filed on, Dec. 10, 2020 which claims the benefit of the filing date to U.S. Provisional Application No. 62/951,425, filed on Dec. 20, 2019, the entire disclosures of which are incorporated by reference herein.

FIELD OF THE INVENTION

This invention belongs to the field of polymer science. In particular, it relates to certain catalysts useful in the methanolysis of poly(ethylene terephthalate) (PET) to form dimethyl terephthalate.

BACKGROUND OF THE INVENTION

The challenge of plastics waste processing is a pressing issue today in the global economy, and chemical companies are faced with the issue of developing a circular economy for their product lines. Poly(alkene terephthalate) polymers are produced in large quantities and deployed in a variety of applications including but not limited to water bottles, textiles, film, and resin. Due to the increased quantities of waste generated from these materials, there is a need to develop improved methods for mechanical or chemical recycling of these waste streams.

While a large majority of the approaches for chemical recycling of PET wastes involves conversion of PET into terephthalic acid (hydrolysis) or bis-hydroxyethyl terephthalate (glycolysis), a number of approaches have also been described for the conversion of PET into dimethyltereph-thalate (DMT) via a process known as methanolysis. The methanolytic depolymerization of PET is catalyzed by a number of typical transesterification promotors, the pre-ferred catalyst in the art for methanolysis has historically been zinc acetate dihydrate [Zn(OAc)$_2$*2H$_2$O]. This catalyst has been generally preferred in the field for the following considerations:

1. Zn(OAc)$_2$*2H$_2$O is inexpensive and easy to obtain.
2. Varied PET waste feeds generally contain certain amounts of water content, which can deactivate water sensitive catalysts. Zn(OAc)$_2$*2H$_2$O is generally water tolerant and not deactivated by residual moisture.
3. Zn(OAc)$_2$*2H$_2$O is, generally speaking, not susceptible to poisoning from residual impurities in PET waste streams from varied sources.

However, despite these advantages, the use of Zn(OAc)$_2$*2H$_2$O also carries with it a number of drawbacks. First, the catalyst generally low in activity, requiring reaction temperatures in excess of 250° C. in a low or high pressure environment. Additionally, a large excess of methanol is generally required to maintain suitable reaction rates (4:1 methanol:PET by mass, 24:1 methanol:PET molar ratio). Significant concerns have also arisen regarding handling of waste streams containing significant concentrations of residual zinc salts. Finally, the use of a Lewis acidic catalyst at elevated temperatures gives rise to the catalysis of undesired side reactions including decarboxylation, radical homolysis, and etherification. In consideration of these factors, there exists a need in PET methanolysis for the identification of new catalysts that effectively promotes the methanolysis of PET wastes in the absences of these disadvantages.

SUMMARY OF THE INVENTION

In general, the invention provides improved catalysts for the methanolysis of poly(C$_2$-C$_4$ alkylene terephthalates), such as poly(ethylene terephthalate)(PET), poly(propylene terephthalate)(PPT), and poly(butylene terephthalate)(PBT). In one aspect, the invention provides a process for depolymerization of a poly(C$_2$-C$_4$ alkylene terephthalate), which comprises contacting a poly(C$_2$-C$_4$ alkylene terephthalate) with methanol and a catalyst chosen from sodium carbonate, magnesium methoxide, 1,8-diazabicyclo[5.4.0]undec-7-ene, and triazabicyclodecene, at a temperature sufficient to effect said depolymerization. The process of the invention can be carried out a substantially lower temperature and requires less methanol than necessary for zinc acetate-catalyzed reactions, and is sufficiently robust to tolerate lower-quality poly(C$_2$-C$_4$ alkylene terephthalate) scrap feeds.

DETAILED DESCRIPTION OF THE INVENTION

In a first aspect, the invention provides a process for depolymerization of a poly(C$_2$-C$_4$ alkylene terephthalate), which comprises contacting a poly(C$_2$-C$_4$ alkylene tereph-thalate) with methanol and a catalyst chosen from potassium carbonate, sodium carbonate, magnesium methoxide, 1,8-diazabicyclo[5.4.0]undec-7-ene ("DBU"), and triazabicy-clodecene ("TBD"), at a temperature sufficient to effect said depolymerization.

In general, the pressure, temperature, and poly(C$_2$-C$_4$ alkylene terephthalate) to methanol mass loading in the reaction can be operated within those ranges known for PET methanolysis. See, for example, U.S. Pat. Nos. 5,498,749; 3,776,945; 3,321,510; 3,037,050; 4,578,502; 3,488,298; 4,63,860; and 5,051,528, incorporated herein by reference.

In general, the methanolysis of the invention may be conducted at temperatures of from about 100° C. to about 180° C. and pressures of about 1 to about 15 atmospheres.

The catalyst loading for the process of the invention is not a critical parameter. In certain embodiments, the catalyst loading is from about 0.005 mole to 0.1 mole of catalyst per mole of poly(C$_2$-C$_4$ alkylene terephthalate).

In certain embodiments, the poly(C$_2$-C$_4$ alkylene tereph-thalate) is poly(ethylene terephthalate).

In certain embodiments, the poly(C$_2$-C$_4$ alkylene tereph-thalate) is poly(propylene terephthalate).

In certain embodiments, the poly(C$_2$-C$_4$ alkylene tereph-thalate) is poly(butylene terephthalate).

As noted above, one consequence of the improved metha-nolysis catalysts of the invention is that the process may be conducted at lower temperatures than with Zn(OAc)$_2$*2H$_2$O.

This invention can be further illustrated by the following examples of certain embodiments thereof, although it will be understood that these examples are included merely for purposes of illustration and are not intended to limit the scope of the invention unless otherwise specifically indicated.

Examples

General: Preliminary experimentation was carried out in 25 mL glass pressure tubes and, where appropriate, 15 mL Parr bomb reactors. Reaction optimization and examination of reaction effectiveness against low-quality feeds was carried out in 100 mL stainless steel autoclaves. Virgin PET Pellets were obtained from Eastman Chemical Company. Curbside bottleflake waste PET was obtained from Polyquest and used as received. Pelletized carpet fiber PET was obtained from Circular Polymers and ground to powder prior to use.

Quantitative Gas Chromatography

Methanolysis products were quantified using two internal standard gas chromatography (GC) methods. Data were obtained using an Agilent 7890 equipped with a 7693A autosampler and two G4513A towers. Samples were prepared by adding a known volume of internal standard solution to a known mass of sample and then derivatizing with N,O-Bis(trimethylsilyl)trifluoroacetamide (BSTFA). They were then chromatographed on two columns—a 60 m×0.32 mm×1.0 micron DB-1701™ (J&W 123-0763) and a 60 m×0.32×1 micron DB-1™ (J&W 123-1063)—using programmed temperature development and flame ionization detection. Five-point calibrations were performed for all major components of interest (dimethyl terephthalate, ethylene glycol, methanol, bis(2-hydroxyethyl) terephthalate, etc.), and other, minor components for which there were no reference standards were quantified by using the response factors for structurally similar compounds.

Gas Chromatography/Mass Spectrometry:

Substance identification was performed using a Thermo Scientific Exactive GC™ (Orbitrap GCMS) equipped with a Thermo 1310 GC and Triplus RSH autosampler. The Thermo Orbitrap GCMS has 60000 mass resolution and <3 ppm mass accuracy within the mass calibration range using PFTBA calibrant (30-614 amu). Substance ID for known compounds was determined through electron ionization (EI) spectrum library search using NIST17, Wiley10, DD2014, and internal databases. Where spectra for unknown compounds did not provide a molecular ion by EI-GCMS, ammonia chemical ionization (CI) was used to determine exact molecular mass. Using the HRAM (high resolution accurate mass) capabilities of the Thermo Exactive GC, molecular formulas for unknowns were calculated. Substance identifications for unknowns were assigned using molecular formulas, knowledge of experiment chemistry, and evaluation of EI spectra. The Thermo Orbitrap GCMS was operated at 60000 mass resolution, a scan range of 30-750 amu, 70 eV electron energy, 250° C. transfer line temperature, 300° C. ion source temperature, and 1.0V C-trap energy offset. Lock masses were used that result from normal column bleed (207.03235, 225.04292, 281.05114, 355.06990) and are present in each analysis. For molecular formula calculations, 3 ppm mass error was used to develop a list of formula candidates which were evaluated based on knowledge of experiment chemistry and evaluation of EI spectra. The GC column was a Thermo TG-5-SILMS™, 30 m×0.25 mm×0.25 micron film (low bleed 5% phenyl equivalent), Thermo P/N 26096-1420. Programmed oven temperature development was used from 40-180° C. at 10° C./minute in the first stage, then to 300° C. at 25° C./minute in the second stage. The final oven temperature was held for 15 minutes for a total run-time of 34 minutes. Sample preparation was performed by adding 1.5 mL methylene chloride to the provided sample, vortex-mixing for 30 seconds, and filtering the sample using a 0.45 micron syringe filter. Injections were made by injecting 0.2 uL sample using the Thermo Triplus RSH autosampler and a split-splitless inlet operated at 260° C. and 13.3:1 split ratio. Column flow was helium at 1.5 mL/minute in constant flow mode without vacuum compensation.

Hydrolysis/Liquid Chromatography:

Chemicals and Materials

Water used in all the experiments was purified by a Milli-Q water purification system (EMD Millipore, Billerica, MA) with resistivity of 18.2 MΩ cm$^{-1}$. HPLC grade acetonitrile and reagent grade dimethyl sulfoxide (DMSO) was from Honeywell (Clearwater, FL). Reagent grade 85% phosphoric acid was received from J. T. Baker (Center Valley, PA). Three hydrolysis reagents were used: Reagent 1 was made by mixing 25% volume percent Tetramethylammonium Hydroxide (TMAH) in methanol and DMSO at 40:60 ratio; Reagent 2 was pure DMSO; Reagent 3 was 30% acetic acid in DMSO. Reagent 1 and Reagent 3 were purchased from Reagents (Charlotte, NC) as pre-mixed solutions. 99% pure TPA standard is an internal manufacturing sample was qualified as an analytical standard. Bisphenol A was 99% pure from Sigma Aldrich (St Louis, MO).

Method Calibration

Weigh out 0.05 (+/−0.01) g of terephthalic acid (TPA) and bis phenol A (BPA) using an analytical balance, record weight in grams to the fourth decimal place. Transfer the solid into a 50.00 mL volumetric flask. Add ~40 mL 50/50 dimethylsulfoxide/acetonitrile (DMSO/CAN) and sonicate until the solid is completely dissolved. Bring the volumetric flask up to volume with more DMSO/ACN and mix well. This solution is the stock solution. Concentration is around 1 mg/mL. Make 100 mg/A, 10 µg/mL and 1 µg/mL calibration solutions by serial dilution. An external calibration curve is generated by plotting the peak area of the TPA and BPA peak against the concentration. Calculation of the TPA and BPA level using the equations below:

$$\text{Wt \% } (TPA) = \frac{TPA \text{ Concentration} \left(\frac{\mu g}{mL}\right) \times 15 \text{ mL}}{\text{Sample Weight (g)} \times \left(\frac{1000000 \text{ }\mu g}{1 \text{ g}}\right)} \times 100\%$$

$$BPA \text{ Content (ppm)} = \frac{BPA \text{ Concentration} \left(\frac{\mu g}{mL}\right) \times 15 \text{ mL}}{\text{Sample Weight (g)} \times \left(\frac{1000000 \text{ }\mu g}{1 \text{ g}}\right)} \times 1000000$$

The calibration range is from 1-100 µg/mL for TPA. For high TPA content samples such as pure PET samples, the TPA concentration in the hydrolysate is considerably above the calibration range. Often the TPA concentration exceeds the solubility limit as well and white solids are observed after hydrolysis. To accurately quantify TPA, high TPA content hydrolysates are further diluted by a factor of 125 by pipetting 0.2 mL of homogenized original hydrolysate in a 25 mL volumetric flask and adding DMSO to bring the flask up to volume. This ensures the TPA concentration in the final sample falls below the upper limit of calibration range even for the samples with highest possible amount of TPA (86.4% TPA in pure PET and 85.6% TPA in pure DMT).

Sample Preparation

Weight 0.05 (+/−0.01) g sample in an 8 dram vial. Record weight accurate to 0.1 mg. Add 5 mL Reagent 1 tetramethyl ammonium hydroxide (TMAH) and 5 mL Reagent 2 (DMSO). Add a flea stir bar, cap the vial and place it in a heat block at 121° C. while stirring for 15 minutes. Take the vial out of the heating block and allow it to cool down to room temperature. Add 5 mL Reagent 3 (acetic acid) to neutralize the solution before vialing it for HPLC analysis. Further dilute with more DMSO if necessary.

HPLC Conditions

TABLE 1

| Chromatography Conditions | | | | | | |
|---|---|---|---|---|---|---|
| Column | Agilent Poroshell EC-C18, 4.6 × 150 mm, 2.7 μm, 600 bar, or equivalent. | | | | | |
| Column Temperature (° C.) | 30 | | | | | |
| Injection Volume (μL) | 5 | | | | | |
| Needle Wash | Once with tetrahydrofuran (THF) | | | | | |
| Mobile Phases | A | 0.14% phosphoric acid in water | | | | |
| | B | Acetonitrile | | | | |
| | C | THF | | | | |
| Pre-run | N/A | | | | | |

| | Time (min) | Flow Rate (mL/min) | A % | B % | C % | Max. Pressure (bar) |
|---|---|---|---|---|---|---|
| Gradient | 0 | 0.9 | 79 | 0 | 21 | 600 |
| | 10 | 0.9 | 79 | 0 | 21 | 600 |
| | 18 | 0.9 | 34 | 45 | 21 | 600 |
| | 18.1 | 0.9 | 14 | 65 | 21 | 600 |
| | 19 | 0.9 | 14 | 65 | 21 | 600 |
| | 19.1 | 0.9 | 79 | 0 | 21 | 600 |
| | 25 | 0.9 | 79 | 0 | 21 | 600 |
| Post-run | N/A | | | | | |

| | | | 60 mm path-length | | |
|---|---|---|---|---|---|
| | Flow Cell Wavelength (nm) | Bandwidth (nm) | | Reference Wavelength (nm) | Reference Bandwidth (nm) |
| DAD Settings | 240 | 10 | | 360 | 80 |
| Data Acquisition Rate | | 5 Hz | | | |
| FLD Settings | λex (nm) | | | 225 | |
| | λem (nm) | | | 310 | |
| | PMT Gain | | | 10 | |
| | Lamp Energy Reference | | | On | |
| | Data Frequency (Hz) | | | 2.31 | |
| Stop Time (min) | | 25 | | | | subsequently removed from the sand bath. The resulting crude material was removed from the bomb and analyzed via the analytical methods described above.

Experimental Procedures:

Sample Procedure for Small Scale Methanolysis in Glass Pressure Tubes:

A 25 mL glass pressure tube was charged with polyethylene terephthalate followed by methanol and a magnetic stirring bar. The catalyst of choice was added, and the pressure vessel was sealed. The vessel was then submerged in an oil bath pre-heated to the desired reaction temperature. The time at which the mixture fully dissolved was noted, and the reaction was held at the target temperature for 4 hours. The pressure vessel was then removed from the oil bath and allowed to cool. The resulting crude material was removed from the pressure tube and analyzed via the analytical methods described above.

Sample Procedure for Small Scale Methanolysis in Parr Bomb:

A 15 mL stainless steel Parr bomb was charged with polyethylene terephthalate followed by methanol and a magnetic stirring bar. The catalyst of choice was added, and the bomb was sealed. The bomb was then placed in a heating mantle on a magnetic stir plate, and the temperature was increased to the desired hold point. These conditions were held for four hours. The bomb was then allowed to cool and Sample Procedure for Catalyst Optimization/Evaluation in High Pressure Autoclaves A 100 mL stainless steel autoclave was charged with polyethylene terephthalate followed by methanol and the catalyst of choice. The autoclave was pressure checked with 500 psig $N_2$, vented, purged three more times with $N_2$ and subsequently sealed. Stirring was set to 500 rpm, and the autoclave was heated to the desired set point and allowed to hold at this condition for four hours. Once the hold time was complete, the autoclave was allowed to cool and subsequently depressurized. The crude product material was removed from the autoclave and analyzed via the methods described above.

Results and Discussion

1. Preliminary Screening:

Our initial screen evaluated a wide range of esterification and transesterification promotors for their ability to facilitate the degradation of virgin PET at reduced temperatures (~150° C.). Our initial set consisted of catalysts reported from academic literature as well as from patent literature on the depolymerization of PET. Advantageously, while there exist a number of reports describing the catalysis of PET hydrolysis and glycolysis, there are substantially fewer reports around the analogous methanolysis process. In an initial screen, Virgin PET was placed in a 25 mL pressure tube (or Parr Bomb if necessary) along with methanol and the desired catalyst. The resulting mixture was heated (generally at 150° C.) for four hours. The time was noted at which the mixture became fully dissolved (unless the reaction was carried out in a Parr bomb in which case a 4 hour hold time was used as a standard), and the final mixture was analyzed via GC. Any material found to be insoluble to the GC method was attributed to unreacted or partially reacted PET. A summary of our initial results is given in Table 2. As expected, attempted methanolysis of PET at 150° C. in the absence of any catalyst gave no reaction. As can be seen from the table, a number of catalysts reported to be active in depolymerization of PET (albeit at elevated temperatures) gave either little or no reactivity in our evaluations. As our screening continued, we identified 6 catalysts as high performers in the reaction as evidenced by their activity on PET at reasonable catalyst loadings and their ability to completely consume PET. These catalysts are sodium methoxide, sodium carbonate, potassium carbonate, magnesium methoxide, DBU, and TBD.

TABLE 2

| | | | | | | % DMT of soluble material (GC) | % Insoluble material (GC) |
|---|---|---|---|---|---|---|---|
| Experiment | Catalyst | Catalyst loading (mol %) | MeOH:PET (w/w) | Temperature (° C.) | Dissolution Time (minutes) | | |
| | | | | Catalyst Evaluation for PET Methanolysis. | | | |
| 1 | None | 0 | 3.33:1 | 150 | Never Dissolved | 0.06 | 68.9 |
| 2 | Sodium Methoxide | 10 | 3.33:1 | 150 | 30 | 65.5 | 0 |
| 3 | Sodium Methoxide | 10 | 3.33:1 | 100 | Never dissolved | 64.34 | 22.9 |
| 4[1] | Sodium methoxide, zinc acetate | 10, 2 | 3.33:1 | 150 | 60 | 50.43 | 3.81 |
| 5 | DBU | 10 | | | 60 | 83.86 | 0.32 |
| 6 | DBU | 5 | 3.33:1 | 170 | 240 | 66.99 | 7.43 |
| 7 | Magnesium methoxide | 10 | 3.33:1 | 150 | Never Dissolved | 89.11 | 65.4 |
| 8 | Magnesium methoxide | 10 | 3.33:1 | 200 | Could not measure | 56.05 | 0.61 |
| 9 | Magnesium methoxide | 5 | 3.33:1 | 200 | Could not measure | 74.25 | 1.31 |
| 10 | TBD | 10 | | | 30 | 68.36 | 2.78 |
| 11 | TBD | 5 | 3.33:1 | 130 | 150 | 72.20 | 3.37 |
| 12 | TMG[2] | 10 | 3.33:1 | | 75 | 59.99 | 0.48 |
| 13 | Triethylamine | 10 | 3.33:1 | 150 | Never dissolved | 42.9 | 96.34 |
| 14 | Triethylamine | 10 | 3.33:1 | 170 | Never dissolved | 63.90 | 82.30 |
| 15[3] | Zinc acetate, N,N-dimethylurea | 10, 10 | 3.33:1 | 150 | Never dissolved | 63.77 | 60.74 |
| 16 | Bmim(ZnCl)$_3$ | 10 | 3.33:1 | 150 | Never dissolved | Did not analyze | Did not analyze |
| 17 | TBD/MSA | 10 | 150 | 150 | Never dissolved | 34.8 | 96.9 |
| 18 | tBuOK | 10 | 150 | 150 | 60 | 51.33 | 9.63 |
| 19 | Na$_2$CO$_3$ | 5 | 2.5:1 | 150 | Never dissolved | 52.7 | 43.27 |
| 20 | Na$_2$CO$_3$ | 10 | 2.5:1 | 160 | Could not measure | 74.20 | 2.78 |
| 21 | NaHCO$_3$ | 10 | 2.5:1 | 150 | Never dissolved | 47.7 | 14.8 |
| 22 | K$_2$CO$_3$ | 10 | 3.33:1 | 150 | 120 | 59.07 | 5.54 |
| 23 | K$_2$SO$_4$ | 10 | 3.33:1 | 150 | Never dissolved | 61.7 | 92.67 |
| 24 | KOH | 5 | 3.33:1 | 150 | Never dissolved | Did not analyze | Did not analyze |
| 25 | NaOH | 5 | 3.33:1 | 150 | Never dissolved | Did not analyze | Did not analyze |
| 26 | Ti(O$^i$Pr)$_4$ | 10 | 3.33:1 | 150 | Never dissolved | 4.41 | 95.89 |

[1]10 mol % sodium methoxide and 2 mol % zinc acetate were combined and used in this experiment.

[2]Promising PET conversion was observed in this case, but a number of by-products associated with catalyst decomposition were observed.

[3]10 mol % zinc acetate and 10 mol % N,N-dimethylurea were used in this experiment.

While all of these catalysts are active at reduced temperatures in comparison to the atmospheric pressure process catalyzed by $Zn(OAc)_2 \cdot 2H_2O$, they are not all active at the same temperature range. For example, DBU and TBD are active on PET at reaction temperatures as low as 100° C. while the carbonate bases are poorly reactive until 140° C. is reached. Magnesium methoxide was found to be inactive until the temperature reached 180° C.

Next, we determined to evaluate catalyst performance on recycled PET bottleflake and increased the reaction scale to 15 grams. We carried out these experiments using a high pressure service lab to increase throughput and consistency of results. Reaction conditions were evaluated and optimized using a sequential SIMPLEX optimization technique, (see, Walters F. H., Parker L. R., Morgan S. L., Deming S. N. *Sequential Simplex Optimization*. Boca Raton, FL: CRC Press LLC, 1991) and the results are described in tables 3-7. Experiments were assessed for the criteria of crude DMT yield and reaction completion (as determined by a subjective rating of GCMS desirability). Ideal parameters sought to minimize catalyst loading, methanol:PET ratio, and reaction temperature. For DBU, it was determined that the best conditions for this operation were Examples 36 and 37.

TABLE 3

| | | | | | | | |
|---|---|---|---|---|---|---|---|
| Catalyst optimization for DBU. | | | | | | | |
| Example No. | Methanol to PET Mass Ratio | Catalyst Loading (mol %) | Temp/ | Reaction Time (hours) | % insoluble material (normalized) | GCMS Desirability (1-5) | DMT Yield |
| 27 | 1.67:1 | 2.50 | 100 | 4 | 16.39 | 3 | 59.15 |
| 28 | 1.67:1 | 2.5 | 140 | 4 | 10.05 | 3 | 75.37 |
| 29 | 3.33:1 | 2.5 | 100 | 4 | 9.73 | 4 | 68.85 |
| 30 | 1.67:1 | 7.5 | 100 | 4 | 4.67 | 4 | 73.37 |
| 31 | 1.67:1 | 5 | 100 | 4 | 20.70 | 3 | 53.69 |
| 32 | 1.67:1 | 5 | 120 | 4 | 3.83 | 2 | 64.93 |
| 33 | 2.5:1 | 7.5 | 100 | 4 | 7.37 | 4 | 74.61 |
| 34 | 2.73:1 | 5.83 | 127 | 4 | 4.35 | 4 | 71.48 |
| 35 | 3:01 | 5 | 100 | 4 | 40.36 | 5 | 42.50 |
| 36 | 2.1:1 | 8.7 | 110 | 4 | 8.69 | 5 | 73.75 |
| 37 | 2.5:1 | 6 | 110 | 4 | 10.68 | 5 | 64.88 |
| 38 | 2.75:1 | 7.5 | 100 | 4 | 15.10 | 3 | 75.20 |
| 39 | 1.67:1 | 7.7 | 122 | 4 | 6.44 | 3 | 62.86 |

TABLE 4

| | | | | | | | |
|---|---|---|---|---|---|---|---|
| Catalyst optimization for TBD. | | | | | | | |
| Example No. | Methanol to PET Mass Ratio | Catalyst Loading (mol %) | Temp. | Reaction Time (hours) | % insoluble material (normalized) | GCMS Desirability (1-5) | DMT Yield |
| 40 | 1.67:1 | 7.50 | 100 | 4 | 10.94 | 3.00 | 60.33 |
| 41 | 1.67:1 | 2.5 | 100 | 4 | 54.11 | 4.00 | 21.63 |
| 42 | 1.67:1 | 2.5 | 140 | 4 | 16.63 | 3.00 | 65.19 |
| 43 | 3.33:1 | 2.5 | 100 | 4 | 5.16 | 4.00 | 65.75 |
| 44 | 1.67:1 | 2.5 | 120 | 4 | 53.91 | 3.00 | 26.31 |
| 45 | 2.5:1 | 7.5 | 100 | 4 | 14.23 | 4.00 | 62.99 |
| 46 | 2.73:1 | 5.83 | 127 | 4 | 10.92 | 4.00 | 66.80 |
| 47 | 3:01 | 5 | 100 | 4 | 8.63 | 5.00 | 60.15 |
| 48 | 3.33:1 | 7.5 | 140 | 4 | 12.65 | 5.00 | 70.96 |
| 49 | 2.5:1 | 6 | 110 | 4 | 45.04 | 4.00 | 38.39 |
| 50 | 2.75:1 | 6 | 100 | 4 | 12.14 | 3.00 | 56.53 |
| 51 | 3.33:1 | 7.5 | 100 | 4 | 19.77 | 5.00 | 59.01 |

For TBD, the best conditions identified were examples 48 and 50.

TABLE 5

| | | | | | | | |
|---|---|---|---|---|---|---|---|
| Comparative Examples -- Catalyst optimization for Sodium Methoxide. | | | | | | | |
| Comparative Example No. | Methanol to PET Mass Ratio | Catalyst Loading (mol %) | Temp. | Reaction Time (hours) | % insoluble material (normalised) | GCMS Desirability (1-5) | DMT Yield |
| 52 | 1.67:1 | 7.50 | 100 | 4 | 19.57 | 4 | 104.89 |
| 53 | 3.33:1 | 2.5 | 100 | 4 | 33.21 | 5 | 21.76 |
| 54 | 1.67:1 | 2.5 | 100 | 4 | 93.49 | 4 | 4.15 |
| 55 | 1.67:1 | 2.5 | 140 | 4 | 31.73 | 2 | 38.64 |
| 56 | 1.67:1 | 5 | 120 | 4 | 66.51 | 4 | 16.51 |

TABLE 5-continued

| | | | | | | | |
|---|---|---|---|---|---|---|---|
| _Comparative Examples -- Catalyst optimization for Sodium Methoxide._ | | | | | | | |
| Comparative Example No. | Methanol to PET Mass Ratio | Catalyst Loading (mol %) | Temp. | Reaction Time (hours) | % insoluble material (normalised) | GCMS Desirability (1-5) | DMT Yield |
| 57 | 1.67:1 | 10 | 100 | 4 | 11.50 | 4 | 59.23 |
| 58 | 2.73:1 | 5.83 | 127 | 4 | 23.02 | 4 | 37.47 |
| 59 | 2.5:1 | 5 | 100 | 4 | 6.57 | 5 | 45.48 |
| 60 | 2.1:1 | 8.7 | 110 | 4 | 9.75 | 5 | 62.22 |
| 61 | 2.5:1 | 6 | 110 | 4 | 13.63 | 4 | 47.33 |
| 62 | 1.67:1 | 7.7 | 122 | 4 | 37.21 | 3 | 37.17 |

For Sodium methoxide, the best conditions identified were examples 52 and 60.

was calculated on the basis of gas chromatographic analysis of the crude reaction products

TABLE 6

| | | | | | | | |
|---|---|---|---|---|---|---|---|
| _Catalyst optimization for Sodium Carbonate._ | | | | | | | |
| Experiment Number | Methanol to PET Mass Ratio | Catalyst Loading (mol %) | Temp. | Reaction Time (hours) | % insoluble material (normalized) | GCMS Desirability (1-5) | DMT Yield |
| 63 | 1.67:1 | 2.50 | 140 | 4 | 0.17 | 3 | 67.81 |
| 64 | 1.67:1 | 7.5 | 140 | 4 | 36.26 | 4 | 45.16 |
| 65 | 3.33:1 | 2.50 | 140 | 4 | 1.82 | 4 | 77.76 |
| 66 | 1.67:1 | 2.50 | 180 | 4 | 3.39 | 3 | 55.69 |
| 67 | 1.67:1 | 5 | 160 | 4 | 4.89 | 3 | 48.12 |
| 68 | 2.2:1 | 2.5 | 153 | 4 | 4.81 | 4 | 58.02 |
| 69 | 2.5:1 | 5 | 140 | 4 | 11.36 | 5 | 61.26 |
| 70 | 2.1:1 | 4.37 | 144 | 4 | 9.31 | 4 | 62.15 |
| 71 | 3:01 | 7.5 | 140 | 4 | 8.61 | 3 | 60.76 |

For sodium carbonate, the best conditions identified were examples 65 and 69.

In summary, these results illustrate that when employed in their optimized conditions for catalyst loading and reaction

TABLE 7

| | | | | | | | |
|---|---|---|---|---|---|---|---|
| _Catalyst optimization for Magnesium Methoxide._ | | | | | | | |
| Experiment Number | Methanol to PET Mass Ratio | Catalyst Loading (mol %) | Temp. | Reaction Time (hours) | % insoluble material (normalized) | GCMS Desirability (1-5) | DMT Yield |
| 72 | 1.67:1 | 2.50 | 220 | 4 | 4.45 | 2 | 54.05 |
| 73 | 1.67:1 | 2.50 | 180 | 4 | 7.97 | 3 | 68.65 |
| 74 | 1.67:1 | 7.5 | 180 | 4 | 0.92 | 4 | 80.87 |
| 75 | 3.33:1 | 2.50 | 180 | 4 | 1.66 | 4 | 67.74 |
| 76 | 1.67:1 | 5 | 180 | 4 | 4.20 | 3 | 70.47 |
| 77 | 2.73:1 | 5.83 | 193 | 4 | 3.82 | 5 | 75.13 |
| 78 | 2.5:1 | 5 | 180 | 4 | 5.61 | 5 | 62.08 |
| 79 | 2.9:1 | 6.25 | 210 | 4 | 9.29 | 3 | 59.55 |

In considering the above results, a common trend emerges regarding the most effective reaction conditions for each catalyst. Specifically, the lowest reaction temperature at which the catalyst is active is generally preferred to maximize desirability. Additionally, DMT yield generally improves as methanol amount or catalyst loading is increased.

Further Experiments Utilizing Lesser Quality Feed Materials.

These experiments were carried out in duplicate in order to mitigate experimental error. As a control experiment, the reaction was also evaluated using 1 mol % $Zn(OAc)_2*2H_2O$ at the requisite temperature of 260° C. Crude DMT yield temperature, Magnesium Methoxide, DBU, TBD, sodium carbonate, and potassium carbonate deliver superior yields of crude DMT relative to Zinc Acetate at its optimized conditions (260° C.).

TABLE 8

| | | | | | |
|---|---|---|---|---|---|
| _Crude DMT Yield Comparison of Catalysts compared to Zinc Acetate in Methanolysis of Pelletized Carpet PET._ | | | | | |
| Example No. | Catalyst | Catalyst Mol % | Reaction Temperature | MeOH:PET mass ratio | Crude DMT yield |
| 80 | Zinc acetate | 1 | 260 | 4:1 | 65 |

TABLE 8-continued

Crude DMT Yield Comparison of Catalysts compared to Zinc
Acetate in Methanolysis of Pelletized Carpet PET.

| Example No. | Catalyst | Catalyst Mol % | Reaction Temperature | MeOH:PET mass ratio | Crude DMT yield |
|---|---|---|---|---|---|
| 81 | Zinc acetate | 1 | 260 | 4:1 | 62 |
| 82 | Magnesium Methoxide | 5 | 180 | 2.5:1 | 69 |
| 83 | Magnesium Methoxide | 5 | 180 | 2.5:1 | 73 |
| 84 | DBU | 8 | 110 | 3:1 | 74 |
| 85 | DBU | 8 | 110 | 3:1 | 78 |
| 86 | TBD | 6 | 110 | 3:1 | 77 |
| 87 | TBD | 6 | 110 | 3:1 | 64 |
| 88 | Sodium Methoxide | 8 | 110 | 3:1 | 55 |
| 89 | Sodium Methoxide | 8 | 110 | 3:1 | 50 |
| 90 | Sodium carbonate | 5 | 140 | 2.5:1 | 88 |
| 91 | Sodium carbonate | 5 | 140 | 2.5:1 | 70 |
| 92 | Potassium carbonate | 5 | 140 | 3:1 | 54 |
| 93 | Potassium carbonate | 5 | 140 | 3:1 | 66 |

As evidence that the above catalysts are not poisoned by impurities native to the feedstock, we collected and analyzed the leftover insoluble material (Table 9). These samples were subjected to global hydrolysis and analyzed via liquid chromatography to identify any remaining terephthalic acid residues. These results were then compared with the residual % DMT of the insoluble materials collected. The difference between the two values was determined to be the amount of residual PET in the sample. As can be seen from the table, the five high-performing catalysts were determined to behave comparably to Zinc Acetate in the ability to achieve full PET conversion at their optimized reaction profiles. It is envisioned that further optimization of reaction conditions for each system will lead to additional yield and selectivity improvement.

TABLE 9

Determination of Extent of Methanolysis with Different Catalysts.

| Example | Catalyst | % DMT of Insolubles (GC_Polyrec) | % TPA of Insolubles after Hydrolysis | % unreacted material |
|---|---|---|---|---|
| 94 | DBU | 0.36 | 5.3 | 4.94 |
| 95 | TBD | 0.07 | 8.9 | 8.83 |
| 96 | Sodium Carbonate | 11.7 | 22.7 | 11 |
| 97 | Magnesium Methoxide | 34.9 | 43.9 | 9 |
| 98 | Potassium Carbonate | 44.8 | 45.7 | 0.9 |
| 99 | Zinc Acetate | 0.22 | 3.6 | 3.8 |

The invention claimed is:

1. A process for methanolytic depolymerization of a poly($C_2$-$C_4$ alkylene terephthalate), which comprises contacting a poly($C_2$-$C_4$ alkylene terephthalate) with methanol and a catalyst chosen from magnesium methoxide, 1,8-diazabicyclo[5.4.0]undec-7-ene, and triazabicyclodecene, at a temperature sufficient to effect said depolymerization, wherein the temperature ranges from about 100° C. to about 180° C.

2. The process of claim 1, wherein the catalyst is magnesium methoxide.

3. The process of claim 1, wherein the catalyst is 1,8-diazabicyclo[5.4.0]undec-7-ene.

4. The process of claim 1, wherein the catalyst is triazabicyclodecene.

5. The process of claim 1, wherein the poly($C_2$-$C_4$ alkylene terephthalate) is poly(ethylene terephthalate).

6. The process of claim 1, wherein the poly($C_2$-$C_4$ alkylene terephthalate) is poly(propylene terephthalate).

7. The process of claim 1, wherein the poly($C_2$-$C_4$ alkylene terephthalate) is poly(butylene terephthalate).

8. The process of claim 1, further comprising the step of isolating dimethyl terephthalate formed therefrom.

9. The process of claim 8 wherein the dimethyl terephthalate is isolated via distillation.

* * * * *